US00PP09725P

United States Patent [19]

Fuess

[11] Patent Number: Plant 9,725

[45] Date of Patent: Dec. 3, 1996

[54] CHRYSANTHEMUM PLANT NAMED 'EMPIRE RHAPSODY'

[76] Inventor: Janet S. Fuess, 22 Country Club Dr., New York Mills, N.Y. 13417

[21] Appl. No.: 519,533

[22] Filed: Aug. 25, 1995

[51] Int. Cl.[6] ..... A01H 5/00

[52] U.S. Cl. ..... Plt./76

[58] Field of Search ..... Plt./76

[56] References Cited

U.S. PATENT DOCUMENTS

P.P. 6,987 8/1989 Fuess ..... Plt./76

P.P. 9,440 1/1996 VandenBerg ..... Plt./76

*Primary Examiner*—Howard J. Locker

*Attorney, Agent, or Firm*—Foley & Lardner

[57] ABSTRACT

A Chrysanthemum plant named Empire Rhapsody particularly characterized by its flat capitulum form; decorative capitulum type; dark red-purple ray floret color; diameter across face of capitulum of 50 to 55 mm when fully opened; spreading branching pattern; natural season flower date of August 27 to 29 when planting rooted cuttings on June 17 to 18 in Salinas, Calif., and September 20 to 26 when planting rooted cuttings June 15 to 21 in Hightstown, N.J.; plant height of 23 to 28 cm when grown in fall under natural daylength with no growth regulators; and durable, uniform performance.

3 Drawing Sheets

The present invention comprises a new and distinct cultivar of Chrysanthemum, botanically known as *Dendranthema grandiflora,* and referred to by the cultivar name Empire Rhapsody.

Empire Rhapsody, identified as 9804 (D91-1), was originated from a cross made by the inventor the inventor Janet S. Fuess in a controlled breeding program in New Hartford N.Y. in October 1990.

The female parent of Empire Rhapsody was the cultivar identified as Empire Symphony, disclosed in U.S. Plant Pat. No. 8,782, and described as a purple decorative garden mum.

The male parent of Empire Rhapsody was an unnamed seedling, identified as C87-61, and described as a red daisy garden mum.

Empire Rhapsody was discovered and selected as one flowering plant within the progeny of the stated cross by Janet S. Fuess in September 1991 in New Hartford, N.Y.

The first act of asexual reproduction of Empire Rhapsody was accomplished when vegetative cuttings were taken from the initial selection in October 1991 in a controlled environment in New Hartford, N.Y. by Janet S. Fuess.

Horticultural examination of controlled flowerings of successive plantings has shown that the unique combination of characteristics as herein disclosed for Empire Rhapsody are firmly fixed and are retained through successive generations of asexual reproduction.

Empire Rhapsody has not been observed under all possible environmental conditions. The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October.

The following traits have been repeatedly observed and are determined to be basic characteristics of Empire Rhapsody, which, in combination, distinguish this Chrysanthemum as a new and distinct cultivar:

1. Flat capitulum form.
2. Decorative capitulum type.
3. Dark red-purple ray floret color.

4. Diameter across face of capitulum of 50 to 55 mm when fully opened.
5. Branching pattern is spreading.
6. Natural season flower date of August 27 to 29 when planting rooted cuttings on June 17 and 18 in Salinas, Calif., and of September 20 to 26 when planting rooted cuttings June 15 to June 21 in Hightstown, N.J.
7. Plant height of 23 to 28 cm when grown in fall under natural daylength with no growth regulators.
8. Durable, uniform performance.

The accompanying photographic drawings show typical inflorescence and leaf characteristics of Empire Rhapsody, with the colors being as nearly true as possible with illustrations of this type.

Sheet 1 is a color photograph of Empire Rhapsody grown in natural season outside conditions in Salinas, Calif.

Sheet 2 is a black and white photograph of three views of the inflorescence of Empire Rhapsody.

Sheet 3 is a black and white photograph showing the upper and under sides of the leaves of Empire Rhapsody at 3 stages of development (mature, intermediate and immature). In sheets 2 and 3 a measuring tape in centimeters has been added.

Of the commercial cultivars known to the inventor, the most similar in comparison to Empire Rhapsody is the cultivar identified as Debonair, disclosed in U.S. Plant Pat. No. 5,324. Reference is made to attached Chart A, which compares certain characteristics of Empire Rhapsody to the same characteristics of Debonair.

Similar traits are capitulum form and type, and branching pattern. The natural season flower date of Empire Rhapsody and Debonair in Salinas, Calif. is comparable. Empire Rhapsody has a dark red-purple ray floret color (R.H.S. 64A), while Debonair has a purple ray floret color. Empire Rhapsody has a smaller diameter of capitulum, an earlier natural season flower date in Hightstown, N.J. and a shorter plant height when compared with Debonair.

In the following description color references are made to The Royal Horticultural Society Colour Chart. The color values were determined on plant material grown as a pinched garden mum grown outdoors in Salinas, Calif. on Aug. 23, 1994.

Classification:

*Botanical.—Dendranthema grandiflora* cv Empire Rhapsody.

*Commercial.*—Flat decorative garden mum.

INFLORESCENCE

A. Capitulum:
*Form.*—Flat.
*Type.*—Decorative.
*Diameter across face.*—50 to 55 mm when fully opened.

B. Corolla of ray florets:
*Color (general tonality from a distance of three meters).*—Dark red-purple.
*Color (upper surface).*—64A.
*Color (under surface)*—80C to 81D.
*Shape.*—Flat, straight, with medium length of corolla tube. The ray floret tip is rounded.

C. Corolla of disc florets:
*Color (mature).*—6B.
*Color (immature).*—6B tinged with 151D.

D. Reproductive organs:
*Androecium.*—Present on disc florets only; scant to no pollen.
*Gynoecium.*—Present on both ray and disc florets.

PLANT

A. General appearance:
*Height.*—23 to 28 cm when grown in fall under natural daylength with no growth regulators.

*Branching pattern.*—Spreading.

B. Foliage:
*Color (upper surface).*—147A.
*Color (under surface).*—147B.
*Shape.*—Very deeply lobed.

CHART A

| Characteristic | Empire Rhapsody | Debonair |
|---|---|---|
| Ray floret color | Dark red- | purple |
| Capitulum form | Flat | Flat |
| and type | Decorative | Decorative |
| Diameter across face of capitulum | 50 to 55 mm | 64 to 70 mm |
| Branching pattern | Spreading | Spreading |
| Natural season flower date: | | |
| in Salinas, CA | Aug 27 to 29 | Aug 26 to 31 |
| in Hightstown, NJ | Sep 20 to 26 | Sep 24 to 30 |
| Plant height: | 23 to 28 cm | 30 to 38 cm |

COMPARISONS MADE OF PLANTS GROWN UNDER NATURAL SEASON OUTDOOR CONDITIONS IN SALINAS, CALIFORNIA AND IN HIGHTSTOWN, NEW JERSEY

I claim:

1. A new and distinct Chrysanthemum plant named Empire Rhapsody, as described and illustrated.

* * * * *

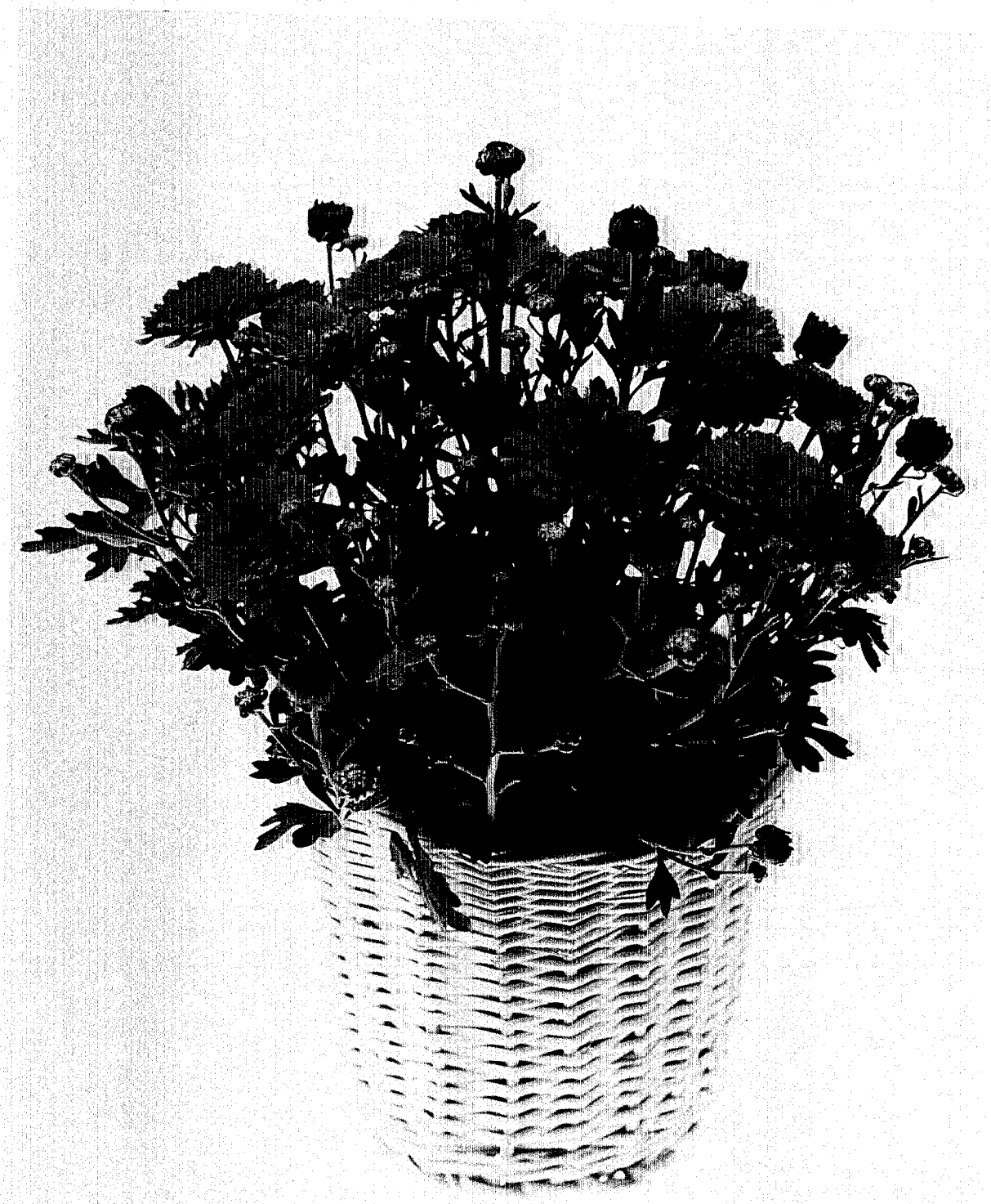

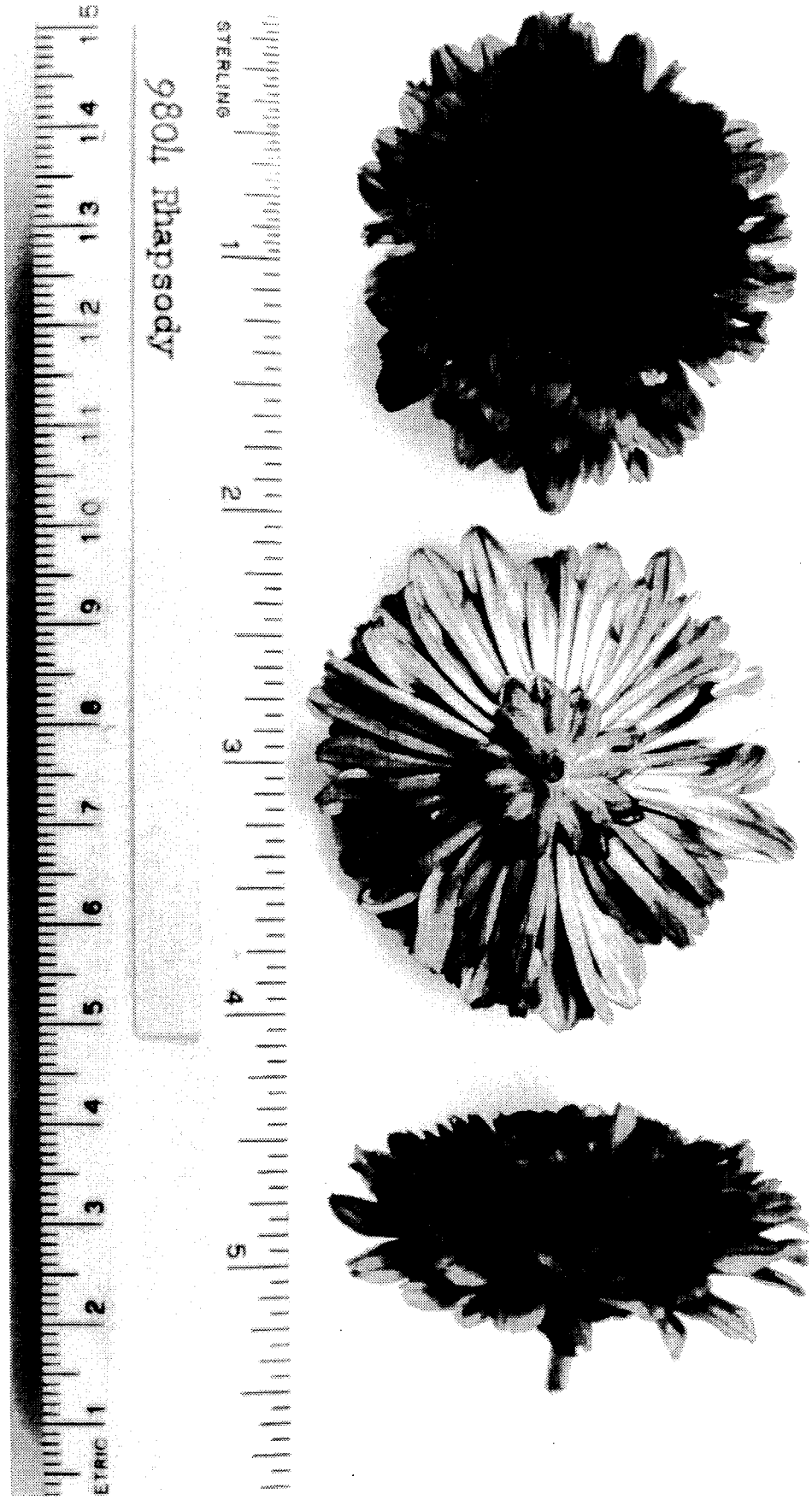
9804 Rhapsody
STERLING
METRIC

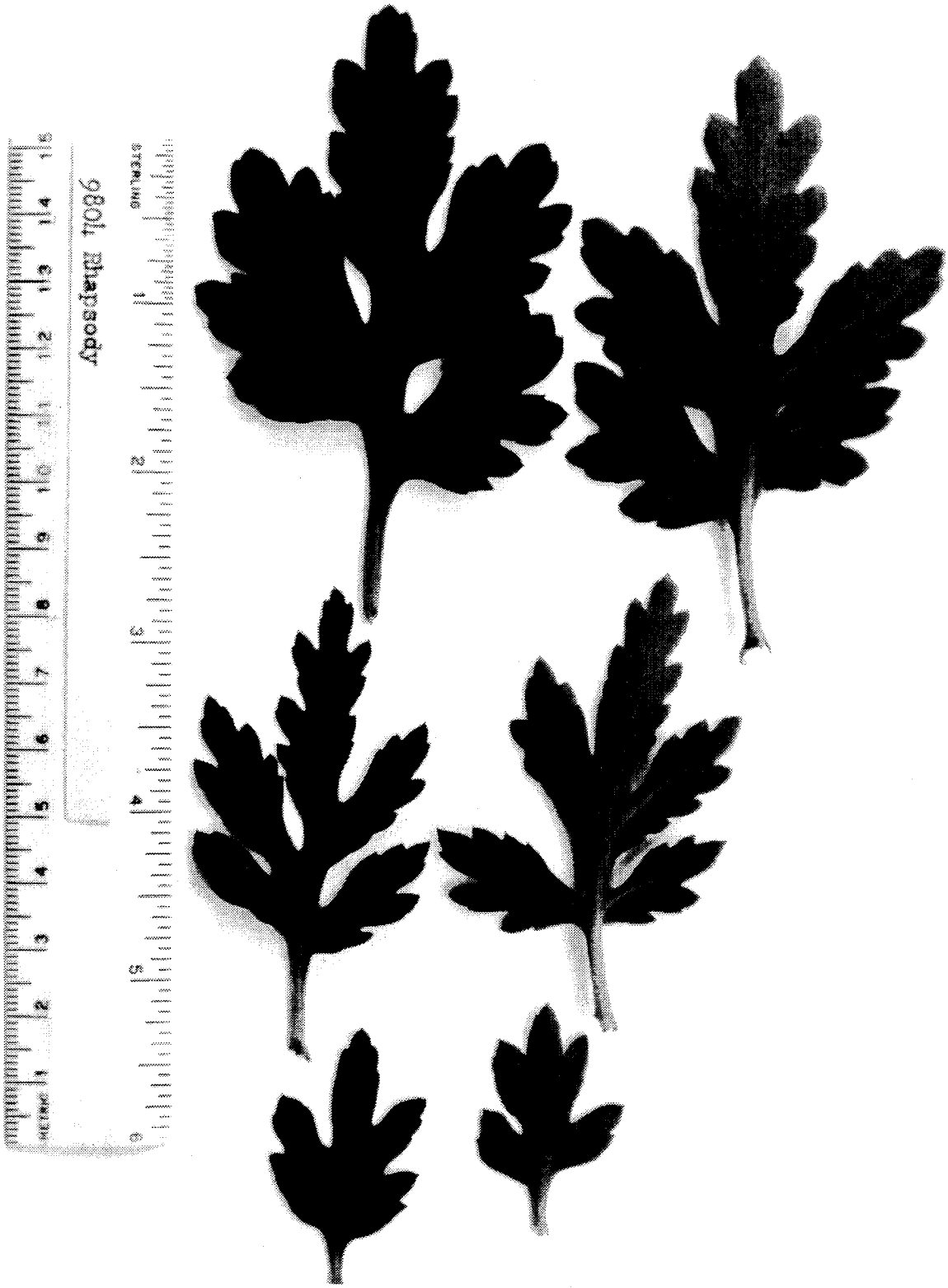
9804 Rhapsody